United States Patent [19]

Neustadt et al.

[11] 4,267,193
[45] May 12, 1981

[54] N-SUBSTITUTED-4-(POLYFLUORO-2-HYDROXY-2-PROPYL)ANILINES AND COMPOUNDS RELATED THERETO

[75] Inventors: Bernard R. Neustadt; Elijah H. Gold, both of West Orange, N.J.

[73] Assignee: Schering Corporation, Kenilworth, N.J.

[21] Appl. No.: 35,962

[22] Filed: May 4, 1979

[51] Int. Cl.$^3$ .................. A01N 37/10; C07C 101/72
[52] U.S. Cl. .................. 424/309; 260/465 E; 424/310; 560/19; 560/49; 562/444; 564/367; 564/369; 564/372; 564/163
[58] Field of Search .............. 562/442, 444; 424/309, 424/310, 452; 560/19, 49

[56] References Cited

U.S. PATENT DOCUMENTS

| | | | |
|---|---|---|---|
| 3,405,177 | 10/1968 | Jones | 260/575 |
| 3,632,636 | 1/1972 | Wei et al. | 562/452 X |
| 3,872,171 | 3/1975 | Cronin et al. | 260/584 |
| 3,978,061 | 8/1976 | Kalopissis et al. | 260/570.5 |
| 4,093,742 | 6/1978 | Neustadt | 260/574 X |

*Primary Examiner*—Robert V. Hines
*Attorney, Agent, or Firm*—Barbara L. Renda; Mary S. King

[57] ABSTRACT

N-substituted-4-(polyfluoro-2-hydroxy-2-propyl)anilines and compounds related thereto, useful as antihypertensive agents, are prepared by reaction of an N-substituted aniline with a polyfluoroacetone.

7 Claims, No Drawings

N-SUBSTITUTED-4-(POLYFLUORO-2-HYDROXY-2-PROPYL)ANILINES AND COMPOUNDS RELATED THERETO

The present invention relates to N-substituted-4-(polyfluoro-2-hydroxy-2-propyl)anilines. More particularly, this invention relates to compounds of the general formula:

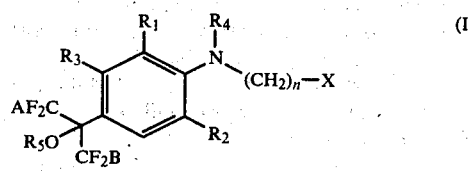

wherein

A and B are independently hydrogen, chloro or fluoro;

$R_1$ is hydrogen, halo, lower alkyl or lower alkoxy;

$R_2$ is halo, lower alkyl or lower alkoxy;

$R_3$ is hydrogen or lower alkyl;

$R_4$ is hydrogen or lower alkyl;

$R_5$ is hydrogen or lower alkyl;

n is 1–3; and

X is cyano, carboxy, lower alkoxycarbonyl, aminocarbonyl, or mono- or di-loweralkylaminocarbonyl when n is 1–3, or amino, mono- or di-loweralkylamino when n is 2–3.

The lower alkyl groups referred to above preferably contain 1–6 carbon atoms and include methyl, ethyl, propyl, butyl, pentyl, hexyl, and the corresponding branched chain isomers thereof. The lower alkoxy groups likewise contain 1–6, and preferably 1–3, carbon atoms and are illustrated by methoxy, ethoxy, n-propoxy, isopropoxy and the like. The term "halo" includes fluoro, chloro, bromo and iodo.

For the purposes of this invention, equivalent to the compounds of formula I when X is amino are the pharmaceutically acceptable acid addition salts thereof. Such acid addition salts may be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic, and related acids. Similarly, the compounds wherein X is carboxy can form amine salts with a variety of pharmaceutically acceptable amines such as procaine or N,N'-dibenzylethylenediamine.

Additionally, the compounds of formula I wherein X is carboxy are capable of forming alkali metal and alkaline-earth metal cationic salts when reacted with equimolar quantities of the appropriate base. For instance, treatment of N-carboxymethyl-2,6-dimethyl-4-(hexafluoro-2-hydroxy-2-propyl)aniline with sodium hydroxide affords the sodium salt of N-carboxymethyl-2,6-dimethyl-4-(hexafluoro-2-hydroxy-2-propyl)aniline. Similarly, the appropriate quantity of potassium or calcium hydroxide affords the potassium or calcium salt.

Preferred compounds of this invention are those wherein $R_1$ and $R_2$ are both methyl or isopropyl. Of these, especially preferred are those wherein n is 1 and X is carboxy, lower alkoxycarbonyl or aminocarbonyl.

The compounds of this invention are useful in view of their pharmacological properties. In particular, they possess activity as antihypertensive agents as evidenced by their ability to reduce blood pressure in animals in which the blood pressure has become abnormally elevated.

The antihypertensive activity of the instant compounds is demonstrated by the results of a standardized test for such activity using male, spontaneously hypertensive rats in which systolic blood pressures and heart rates are recorded by the semi-automated indirect precedure of Vaynofsky. Among the compounds of this invention which have been found particularly active in this test are the representative compounds N-(2-aminoethyl)-2,6-dimethyl-4-(hexafluoro-2-hydroxy-2-propyl)aniline; N-ethoxycarbonylmethyl-2,6-dimethyl-4-(hexafluoro-2-hydroxy-2-propyl)aniline; N-carboxymethyl-2,6-diisopropyl-4-(hexafluoro-2-hydroxy-2-propyl)aniline and N-aminocarbonylmethyl-2,6-dimethyl-4-(hexafluoro-2-methoxy-2-propyl)aniline. Other compounds found active in this test procedure are those such as N-(2-cyanoethyl)-2,6-dimethyl-4-(hexafluoro-2-hydroxy-2-propyl) aniline, N-(3-aminopropyl)-2,6-dimethyl-4-hexafluoro-2-hydroxy-2-propyl)aniline and ethyl[2,6-dimethyl-4-(tetrafluoro-1,3-dichloro-2-hydroxy-2-propyl)anilino]acetate.

In view of their potent pharmacological properties, the compounds of this invention can be combined with pharmaceutical carriers and administered in a variety of well-known pharmaceutical forms suitable for oral or parenteral administration to provide compositions useful in the treatment of cardiovascular disorders, and particularly, mammalian hypertension.

Based upon laboratory tests, the effective dose ($ED_{50}$) of the compounds of this invention will typically be in the range of about 0.5 to about 100 mg/kg, preferably about 5–25 mg/kg, of mammalian weight administered in single or divided doses. The exact dose to be administered is dependent upon where the particular compound lies within the above quoted range, as well as upon the age, weight and condition of the individual.

The compositions containing the compounds of this invention will preferably contain from about 25 to about 500 mg of the active compound per dosage unit. They may be administered parenterally but are most preferably administered orally. Typical formulations are those such as tablets, capsules, syrups, elixirs or suspensions.

Typical acceptable pharmaceutical carriers for use in formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose, and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid vegetable oils such as peanut oil, cottonseed oil, sesame oil, olive oil and corn oil; non-ionic, cationic and anionic surfactants; ethylene glycol polymers; β-cyclodextrin; fatty alcohols and hydrolyzed cereal solids; as well as other non-toxic compatible fillers, binders, disintegrants and lubricants commonly used in pharmaceutical formulations.

In treating certain patients with the compounds of this invention, it may be desirable to include other pharmaceutically active ingredients in the same dosage unit. For example, in treating patients in whom salt and water retention is a problem, effective amounts of conventional diuretics, e.g., hydrochlorothiazide or trichloromethiazide, may be added.

The compounds of formula I wherein X is other than carboxy and $R_5$ is hydrogen may be conveniently prepared by reaction of a compound of the formula

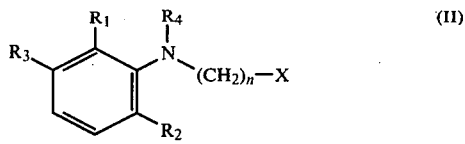

wherein X is cyano, amino, lower alkoxycarbonyl, aminocarbonyl or mono- or di-loweralkylaminocarbonyl, and n, $R_1$, $R_2$, $R_3$ and $R_4$ are as hereinabove defined, with a polyfluoroacetone of the formula

wherein A and B are as hereinbefore defined or a hydrate thereof. The reaction may be carried out in the presence or absence of a catalyst. Preferably, a sulfonic acid catalyst, such as p-toluenesulfonic acid, is utilized to enable the reaction to proceed at a faster rate. When used, the catalyst is employed in an amount from about 0.1 to 10% by weight, based on the amount of the compound of formula II used.

The reaction may be carried out in the presence or absence of a solvent. If a solvent is used, it is typically an inert organic solvent such as benzene, xylene or chlorobenzene.

Typical reaction times are from about 5–36 hours, and typical reaction temperatures are from about room temperature to about 150° C., with times of about 16 hours and temperatures of about 50°–150° C. being preferred.

Preparable from the appropriate starting materials by this reaction scheme are the following compounds of this invention:

N-(2-cyanoethyl)-2,6-dimethyl-4-(hexafluoro-2-hydroxy-2-propyl)aniline;
N-(2-cyanoethyl)-2,3,6-trimethyl-4-(hexafluoro-2-hydroxy-2-propyl)aniline;
N-(2-cyanoethyl)-2,6-dichloro-4-(hexafluoro-2-hydroxy-2-propyl)aniline;
N-methyl-N-(2-cyanoethyl)-2,6-dimethyl-4-(hexafluoro-2-hydroxy-2-propyl)aniline;
N-(2-cyanoethyl)-2,6-diethyl-4-(1,1,3,3-tetrafluoro-2-hydroxy-2-propyl)aniline;
N-(2-cyanoethyl)-2,6-dimethyl-4-(1,1,3,3-tetrafluoro-1,3-dichloro-2-hydroxy-2-propyl)aniline;
N-cyanomethyl-2,6-dimethyl-4-(1,1,3,3-tetrafluoro-2-hydroxy-2-propyl)-aniline;
N-(3-aminopropyl)-2,6-dimethyl-4-(hexafluoro-2-hydroxy-2-propyl)aniline;
N-(3-aminopropyl)-2,3,6-trimethyl-4-(hexafluoro-2-hydroxy-2-propyl)aniline;
N-(3-aminopropyl)-2,6-dichloro-4-(hexafluoro-2-hydroxy-2-propyl)aniline;
N-methyl-N-(3-aminopropyl)-2,6-dimethyl-4-(hexafluoro-2-hydroxy-2-propyl)aniline;
N-(3-aminopropyl)-2,6-diethyl-4-(1,1,3,3-tetrafluoro-2-hydroxy-2-propyl)aniline;
N-(3-aminopropyl)-2,6-dimethyl-4-(1,1,3,3-tetrafluoro-1,3-dichloro-2-hydroxy-2-propyl)aniline;
N-(2-aminoethyl)-2,6-dimethyl-4-(hexafluoro-2-hydroxy-2-propyl)aniline;
N-ethoxycarbonylmethyl-2,6-dimethyl-4-(hexafluoro-2-hydroxy-2-propyl)aniline;
N-ethoxycarbonylmethyl-2,6-dibromo-4-(hexafluoro-2-hydroxy-2-propyl)aniline;
N-ethoxycarbonylmethyl-2-isopropyl-4-(hexafluoro-2-hydroxy-2-propyl)aniline;
N-ethoxycarbonylmethyl-2,6-diisopropyl-4-(hexafluoro-2-hydroxy-2-propyl)aniline;
N-n-propoxycarbonylmethyl-2,6-dimethyl-4-(hexafluoro-2-hydroxy-2-propyl)aniline;
N-ethoxycarbonylmethyl-2,6-dimethyl-4-(1,1,3,3-tetrafluoro-2-hydroxy-2-propyl)aniline;
N-ethoxycarbonylmethyl-2,6-dimethyl-4-(1,1,3,3-tetrafluoro-1,3-dichloro-2-hydroxy-2-propyl)aniline;
N-(aminocarbonylmethyl)-2,6-dimethyl-4-(hexafluoro-2-hydroxy-2-propyl)aniline;
N-(aminocarbonylmethyl)-2,6-dichloro-4-(hexafluoro-2-hydroxy-2-propyl)aniline;
N-(aminocarbonylmethyl)-3,6-dimethyl-4-(hexafluoro-2-hydroxy-2-propyl)aniline;
N-(aminocarbonylmethyl)-2,6-diisopropyl-4-(hexafluoro-2-hydroxy-2-propyl)aniline;
N-(2-aminoethyl)-2,6-dimethyl-4-(hexafluoro-2-hydroxy-2-propyl)aniline;
N-(dimethylaminoethyl)-2,6-dimethyl-4-(hexafluoro-2-hydroxy-2-propyl)aniline;
N-(methylaminoethyl)-2,6-dimethyl-4-(hexafluoro-2-hydroxy-2-propyl)aniline.

The compounds of formula I wherein X is carboxy may be prepared by hydrolysis of the corresponding compound wherein X is lower alkoxycarbonyl. This is most preferably accomplished using a strong base such as sodium or potassium hydroxide.

Preparable by this route are the following representative compounds of this invention:

N-(2-carboxyethyl)-2,6-dimethyl-4-(hexafluoro-2-hydroxy-2-propyl)aniline;
N-carboxymethyl-2,6-dimethyl-4-(hexafluoro-2-hydroxy-2-propyl)aniline;
N-carboxymethyl-2,6-diisopropyl-4-(hexafluoro-2-hydroxy-2-propyl)aniline;
N-carboxymethyl-2,6-dichloro-4-(hexafluoro-2-hydroxy-2-propyl)aniline;
N-carboxymethyl-2,6-dimethyl-4-(1,1,3,3-tetrafluoro-1,3-dichloro-2-hydroxy-2-propyl)aniline.

Alternatively, the compounds of formula I wherein X is lower alkoxycarbonyl may be prepared by reaction of a compound of the formula

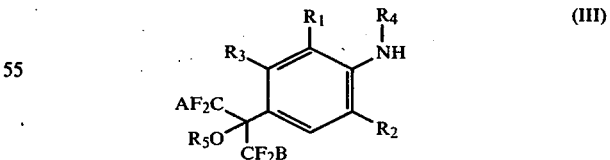

wherein A, B, $R_1$, $R_2$, $R_3$, $R_4$ and $R_5$ are as hereinbefore defined with a halo ester of the formula

wherein n is as hereinabove defined and Hal is chloro or bromo. Typical solvents are those such as acetonitrile and dimethylformamide. Reaction temperatures vary from about 50° C. to the reflux temperature of the solvent, and times vary from 12–36 hours depending upon the nature of the reactants.

Compounds of formula I wherein X is aminocarbonyl, mono-alkylaminocarbonyl or di-alkylaminocarbonyl may also be prepared by reaction of compounds of formula I wherein X is lower alkoxycarbonyl or carboxy with the appropriately substituted amine by methods well known in the art.

An alternate route to the compounds wherein X is amino or mono- or di-lower alkylamino involves the reaction of a compound of the formula

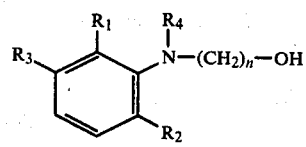

with the polyfluoroacetone according to the above described (page 5) procedure. The primary hydroxy group of the resulting intermediate of the formula

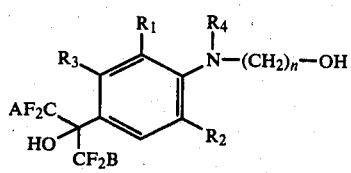

is then replaced by a chloro or bromo by a conventional halogenating agent, e.g., thionyl chloride, which is then reacted with ammonia or the desired mono- or di-lower alkyl amine to afford the desired compound.

The compounds of formula I wherein $R_5$ is lower alkyl may be prepared by contacting the compounds of formula I wherein $R_5$ is hydrogen with a strong base such as sodium hydride and adding an appropriate lower alkyl halide. The halide is preferably the iodide, but the bromides and the chlorides may also be used. The reaction is preferably conducted in a polar, aprotic solvent such as dimethylformamide or dimethylsulfoxide.

The starting materials of formula II wherein X is aminocarbonyl or mono- or di-loweralkylaminocarbonyl are prepared by reaction of the appropriate 2,3,6-trisubstituted aniline with an appropriately substituted 2-chloroacetamide, 3-chloropropionamide or 4-chlorobutyramide in the presence of an acid acceptor. Typically, potassium carbonate is utilized as the acid acceptor, but other organic or inorganic bases may also be used. A polar, aprotic solvent such as dimethylformamide may be optionally utilized, depending upon the nature of the starting reactants. Reaction times vary from about 12 hours to several days and temperatures of from about room temperature to about 150° C. are suitable.

The starting materials of formula II wherein X is amino and n is 3 are prepared by reduction of the appropriate N-(2-cyanoethyl)2,3,6-trisubstituted aniline [preparable according to the procedure of Heininger, *Organic Synthesis*, Coll. Vol. IV, N. Rabjohn, ed., p. 146 (1963)]. Suitable reducing agents are those such as lithium aluminum hydride, diborane and hydrogen with a catalyst. Suitable catalysts are those such as rhodium/aluminum oxide and palladium/carbon. Typically, the reaction is conducted in a polar solvent such as methanol or ethanol.

The following examples describe in detail compounds illustrative of the present invention and methods which have been devised for their preparation. It will be apparent to those skilled in the art that many modifications, both of materials and methods, may be practiced without departing from the purpose and intent of this disclosure.

EXAMPLE 1

N-(2-Cyanoethyl)-2,6-Dimethyl-4-(Hexafluoro-2-Hydroxy-2-Propyl)Aniline

Combine N-(2-cyanoethyl)-2,6-dimethylaniline (40 g, 0.23 mol) and hexafluoroacetone sesquihydrate (97 g, 0.50 mol) with 1.0 g p-toluenesulfonic acid and reflux 6 hours. Add more hexafluoroacetone sesquihydrate (48 g, 0.25 mol) and reflux 16 hours. Allow to cool, pour onto water, and collect the solid. Dissolve the solid in ether, dry and concentrate. Recrystallize from ether-hexane to obtain the title compound as a white solid, m.p. 111°–114° C.

EXAMPLE 2

N-(3-Aminopropyl)-2,6-Dimethyl-4-(Hexafluoro-2-Hydroxy-2-Propyl)Aniline

To a solution of N-(2-cyanoethyl)-2,6-dimethylaniline (25.0 g, 0.144 mol) in 200 ml 4 N ethanolic ammonia add 3.0 g 5% rhodium/aluminum oxide. Hydrogenate 3 days at 50 psi. Filter, concentrate, distill and collect a fraction of b.p. 85°–90° C./0.1 mm, N-(3-aminopropyl)-2,6-dimethylaniline.

Combine the above N-(3-aminopropyl)-2,6-dimethylaniline (13.0 g, 73 mmol) with hexafluoroacetone sesquihydrate (58.0 g, 0.3 mol) and 1.0 g p-toluenesulfonic acid. Reflux 16 hours and allow to cool. Pour onto water and add $Na_2CO_3$ until basic. Extract with ether and wash ether extracts with 1.0 N HCl. Basify the aqueous solution with $Na_2CO_3$ and extract with ether. Dilute the ether extracts with an equal volume of hexane. Extract with 1.0 N NaOH. Neutralize to pH 8 and extract with ether. Dry and concentrate. Subject the solid to sublimation at 130°/0.1 mm. Wash the sublimation residue with hot ether to obtain the product, N-(3-aminopropyl)-2,6-dimethyl-4-(hexafluoro-2-hydroxy-2-propyl)aniline as a solid, m.p. 130°–133° C.

EXAMPLE 3

N-Ethoxycarbonylmethyl-2,6-Dimethyl-4-(Hexafluoro-2-Hydroxy-2-Propyl)Aniline

Combine ethyl N-ethoxycarbonylmethyl-2,6-dimethylaniline (10.4 g, 50 mmol) with hexafluoroacetone sesquihydrate (20 g, 100 mmol) and 0.2 g p-toluenesulfonic acid. Reflux 5 hours, allow to cool, and pour onto water. Decant, and partition the oil between ether and water. Wash with 1.0 N HCl, then 1.0 N NaHCO₃. Dry and concentrate. Recrystallize from ether-hexane and sublime at 80° C./0.1 mm. Recrystallize the sublimate from ethanol-water, then benzene-hexane to give the title compound as a white solid, m.p. 91°–93° C.

EXAMPLE 4

N-Ethoxycarbonylmethyl-2,6-Diisopropyl-4-(Hexafluoro-2-Hydroxy-2-Propyl)Aniline

A. Dissolve 2,6-diisopropylaniline (53.1 g, 0.30 mol) and ethyl bromoacetate (55.1 g, 0,33 mol) in 200 ml DMF. After 72 hours, pour onto aqueous NaHCO$_3$ and extract with hexane. Wash the hexane twice with water. Dry, concentrate and distill to obtain as a fraction b.p. 130°–145° C./0.1 mm N-ethoxycarbonylmethyl-(2,6-diisopropyl)aniline.

B. Combine the N-ethoxycarbonylmethyl-(2,6-diisopropyl)aniline (26.3 g, 0.100 mol) with hexafluoroacetone sesquihydrate (38.6 g, 0.20 mol) and 1.0 g toluenesulfonic acid. Reflux 20 hours, allow to cool, and pour onto water. Extract with ether, dry, and concentrate. Warm with hexane and allow to cool to obtain the product, N-ethoxycarbonylmethyl-2,6-diisopropyl-4-(hexafluoro-2-hydroxy-2-propyl)aniline, as a solid, m.p. 72°–73° C.

EXAMPLE 5

N-Aminocarbonylmethyl-2,6-Dimethyl-4-(Hexafluoro-2-Hydroxy-2-Propyl)Aniline

A. Add 200 ml dimethylformamide to a mixture of 2,6-dimethylaniline (36.3 g, 0.30 mol), 2-chloroacetamide (74.8 g, 0.80 mol) and potassium carbonate (41.4 g, 0.3 mol). Heat at 120° for 72 hours, allow to cool, and pour into water. Extract with 1:1 ether-ethyl acetate. Wash the organic with 1.0 N HCl. Neutralize the aqueous layer with NaHCO$_3$ and extract it with ethyl acetate. Dry, concentrate, and distill to collect a fraction, b.p. 157°–167°/0.1 mm. Recrystallize from methylene chloride-hexane to give as a solid, m.p. 91°–92°, N-aminocarbonylmethyl-2,6-dimethylaniline.

B. Combine the above N-aminocarbonylmethyl-2,6-dimethylaniline (4.0 g, 22 mmol) with hexafluoroacetone sesquihydrate (8.5 g, 44 mmol) and 0.2 p-toluenesulfonic acid. Reflux 6 hours, cool and pour onto water. Filter the solid, dissolve in ethyl acetate, dry, and concentrate. Recrystallize from methanol-water to give the N-aminocarbonylmethyl-2,6-dimethyl-4-(hexafluoro-2-hydroxy-2-propyl)aniline, as a white solid, m.p. 205°–207° C.

EXAMPLE 6

N-(2-Aninoethyl)-2,6-Dimethyl-4-(Hexafluoro-2-Hydroxy-2-Propyl)Aniline

A. Combine N-(2-hydroxyethyl)-2,6-dimethylaniline (49.5 g, 0.30 mol) with the hexafluoroacetone sesquihydrate (135 g, 0.70 mol) and 1.0 g p-toluenesulfonic acid. Reflux 16 hours, allow to cool, and pour onto water. Add Na$_2$CO$_3$ to pH 10. Filter the solid, dissolve in ether, dry and concentrate. Recrystallize from ether-hexane to give solid, m.p. 110°–113° C., N-(2-hydroxyethyl)-2,6-dimethyl-4-(hexafluoro-2-hydroxy-2-propyl)aniline.

B. Dissolve the N-(2-hydroxyethyl)-2,6-dimethyl-4-(hexafluoro-2-hydroxy-2-propyl)aniline (40.0 g, 0.12 mol) in 300 ml CHCl$_3$. Add a solution of SOCl$_2$ (59.5 g, 0.50) in 100 ml CHCl$_3$. Reflux 16 hours, allow to cool, and dilute with an equal volume of hexane. Filter to give solid, m.p. 190°–196° C. (dec.), N-(2-chloroethyl)-2,6-dimethyl-4-(hexafluoro-2-hydroxy-2-propyl)aniline hydrochloride. The corresponding free base has m.p. 101°–104° C.

C. Dissolve N-(2-chloroethyl)-2,6-dimethyl-4-(hexafluoro-2-hydroxy-2-propyl)aniline hydrochloride (19.3 g, 50 mmol) in 100 ml ethanol, and bubble in NH$_3$ (8.5 g, 0.50 mol). Heat in a steel bomb 16 hours at 100°. Let cool and partition between ether and water. Extract the ether with 1.0 N HCl. Basify the aqueous with Na$_2$CO$_3$, extract with ether, dry and concentrate. Recrystallize from ether-hexane to give the title compound as a solid product, m.p. 158°–161° C.

EXAMPLE 7

N-(Dimethylaminoethyl)-2,6-Dimethyl-4-(Hexafluoro-2-Hydroxy-2-Propyl)Aniline

Dissolve the chloroethyl hydrochloride of Example 6B (10.0 g=26 mmol) in 200 ml ethanol. Heat to reflux and bubble in dimethylamine over 4 hours. Allow to cool, concentrate, and partition between Et$_2$O and water. Extract the Et$_2$O with 1.0 N HCl. Basify the aqueous with Na$_2$CO$_3$, extract with Et$_2$O, dry, concentrate and recrystallize from Et$_2$O-hexane to give the title product as a white solid, melting at about 112°–115° C.

EXAMPLE 8

N-Ethoxycarbonylmethyl-2,6-Dimethyl-4-(Tetrafluoro-1,3-Dichloro-2-Hydroxy-2-Propyl)Aniline Combine 2,6-dimethyl-4-(tetrafluoro-1,3-dichloro-2-hydroxy-2-propyl)aniline [Gilbert, et. al., *J. Org. Chem.*, 30, 1001 (1965)] (26 g=0.08 mol) with ethyl bromoacetate (22 g=0.13 mol) and potassium iodide (22 g=0.13 mol) in 150 ml CH$_3$CN. Heat to reflux and add NaHCO$_3$ (13.4 g=0.16 mol). Heat at reflux 20 hours, allow to cool, pour onto water, and extract with Et$_2$O. Wash the Et$_2$O with 10% Na$_2$CO$_3$, then 1 N HCl. Dry over MgSO$_4$ and filter. Add 4 N HCl/Et$_2$O and dilute with an equal volume of hexane. Decant and wash the solid with benzene. Partition the solid between 10% Na$_2$CO$_3$ and Et$_2$O. Dry and concentrate the Et$_2$O. Recrystallize the residue from hexane to obtain the title product as a white solid, melting at about 102°–104° C.

EXAMPLE 9

N-(2-Carboxyethyl)-2,6-Dimethyl-4-(Hexafluoro-2-Hydroxy-2-Propyl)Aniline

Combine N-(2-cyanoethyl)-2,6-dimethyl-4-(hexafluoro-2-hydroxy-2-propyl)aniline (4.0 g, 12 mmol) with 350 ml 1.0 N NaOH. Reflux 2 hours, allow to cool, add concentrated HCl, and then solid NaHCO$_3$. Extract with ether, dry and concentrate. Recrystallize from ether-hexane to give title compound as a solid product, m.p. 175°–176° C.

EXAMPLE 10

N-Carboxymethyl-2,6-Dimethyl-4-(Hexafluoro-2-Hydroxy-2-Propyl)Aniline

Dissolve ethyl N-[2,6-dimethyl-4-(hexafluoro-2-hydroxy-2-propyl)phenyl]glycinate (3.1 g, 8.3 mmol) in 25 ml 1.0 N NaOH. After 1 hour, add 25 ml 1.0 N HCl and extract with ethyl acetate. Dry and concentrate. Recrystallize from chloroform-benzene to give the title compound as beige solid, m.p. 153°–155° C. dec.

EXAMPLE 11

N-Carboxymethyl-2,6-Diisopropyl-4-(Hexafluoro-2-Hydroxy-2-Propyl)Aniline

Stirr ethyl N-[2,6-diisopropyl-4-(hexafluoro-2-hydroxy-2-propyl)phenyl]glycinate (5.0 g, 12 mmol) with 50 ml 1.0 N NaOH for 1 hour. Neutralize the solution with 50 ml 1.0 N HCl. Filter the solid, dissolve in ether, dry and concentrate. Recrystallize from ether-hexane to obtain the title compound as a white solid, m.p. 130°–132° C.

EXAMPLE 12

N-Carboxymethyl-2,6-Dimethyl-4-(Tetrafluoro-1,3-Dichloro-2-Hydroxy-2-Propyl)Aniline Dissolve the ethyl ester of Example 8 (3.0 g=7.4 mmol) in 70 ml 1.0 N NaOH. After 30 minutes acidify with concentrated HCl to pH 4. Extract the product with Et$_2$O, dry and concentrate. Recrystallize from Et$_2$O-hexane to obtain the title product as a white solid, melting at about 139°–142° (dec.)

What is claimed is:

1. A compound of the formula

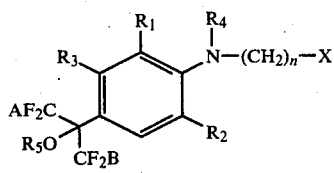

wherein

A and B are independently hydrogen, chloro or fluoro;
R$_1$ is hydrogen, halo, lower alkyl or lower alkoxy;
R$_2$ is halo, lower alkyl or lower alkoxy;
R$_3$ is hydrogen or lower alkyl;
R$_4$ is hydrogen or lower alkyl;
R$_5$ is hydrogen or lower alkyl;
n is 1–3; and
X is carboxy; and the pharmaceutically acceptable salts thereof.

2. A compound according to claim 1 wherein R$_1$ and R$_2$ are both methyl.

3. A compound according to claim 2 which is N-(2-carboxyethyl)-2,6-dimethyl-4-(hexafluoro-2-hydroxy-2-propyl)aniline.

4. A compound according to claim 2 which is N-carboxymethyl-2,6-dimethyl-4-(hexafluoro-2-hydroxy-2-propyl)aniline.

5. A compound according to claim 1 which is N-carboxymethyl-2,6-diisopropyl-4-(hexafluoro-2-hydroxy-2-propyl)aniline.

6. A method of treating hypertension which comprises administering to a hypertensive mammal an antihypertensive amount of a compound of claim 1.

7. A pharmaceutical composition for use in the treatment of hypertension which comprises an antihypertensive amount of a compound of claim 1 in admixture with a pharmaceutical carrier therefor.

* * * * *